United States Patent
Rende

[11] 3,934,462
[45] Jan. 27, 1976

[54] AUTOMATIC COMPUTING OCULAR TONOMETER SYSTEM

[75] Inventor: Richard F. Rende, Maywood, Ill.

[73] Assignee: American Hospital Supply Corporation, Evanston, Ill.

[22] Filed: Sept. 6, 1974

[21] Appl. No.: 503,950

[52] U.S. Cl. ................................. 73/80; 235/151.3
[51] Int. Cl.² .......................................... A61B 3/16
[58] Field of Search ...................... 73/80; 235/151.3

[56] References Cited
UNITED STATES PATENTS
3,677,074    7/1972    Murr .......................................... 73/80

Primary Examiner—Jerry W. Myracle
Attorney, Agent, or Firm—Dawson, Tilton, Fallon & Lungmus

[57] ABSTRACT

A transducer, placed on an eye being tested, generates an analog signal representative of pressure. The analog signal is periodically converted to digital signals in binary coded decimal representation. Each test is carried out under control of a computer driven by a real time clock which is actuated in response to placing the tonometer in test position on an eye. The computer takes the tonometer measurements at predetermined times as determined by the real time clock, and stores the data in a random access memory, together with signals representative of other important test parameters. From this data, the computer calculates intraocular pressure, the coefficient of outflow value and the flow value, which are also stored in the memory. A visual display unit is associated with the memory for displaying the tonometer measurement data, test parameters and computed results. Test measurements and other test parameters may also be loaded into the system by a manually operated keyboard for computation and display. The computation takes into account many of the artifacts which previously has decreased accuracy. A pair of signal lights on the handpiece are energized by control logic for indicating to the clinician the exact status of the test whether the results being obtained are satisfactory, and whether current or old test data is stored in the memory, without having to divert his attention from the handpiece placed on the eye.

22 Claims, 10 Drawing Figures

FIG.3

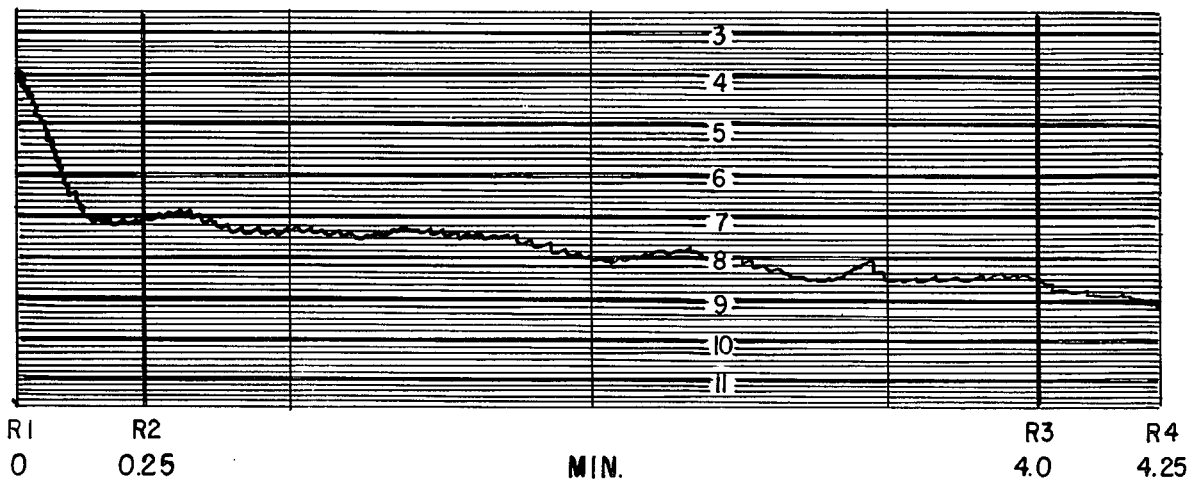

R1         R2                                                  R3      R4
0          0.25                      MIN.                       4.0    4.25

FIG. 6

| | RED LED | GREEN LED | |
|---|---|---|---|
| LL1 | ○ | ○ | COMPUTER CLEAR READY TO START TEST |
| LL2 | (on) | ☀ | TEST IN PROGRESS BUT OLD DATA NOT CLEARED |
| LL3 | ○ | ☀ | TEST IN PROGRESS WITH GOOD HEART PULSE |
| LL4 | ○ | ● | TEST IN PROGRESS BUT WITH NO HEART PULSE |
| LL5 | ☀ | ● | BAD TONOGRAM STOP TEST |
| LL6 | ● | ☀ | TEST PERIOD OVER BUT CONTINUING TEST |
| LL7 | ● | ○ | ALL DATA COMPLETE TEST-OVER READ RESULTS. |

FIG.7

| BINARY VALUE | PARAMETER LABEL | READING |
|---|---|---|
| 0000 | R1 | INTITAL TONOGRAPH READING |
| 0001 | R2 | TEST READING |
| 0010 | R3 | FINAL READING |
| 0011 | R4 | EXTENDED FINAL READING |
| 0100 | CC | CORNEAL CURATURE |
| 0101 | OR | OCULAR RIGIDITY |
| 0110 | AR | APPLANATION READING |
| 0111 | T1 | 1ST TIME VALUE |
| 1000 | T2 | 2ND TIME VALUE |
| 1001 | D1 | 1ST DIFF. VALUE |
| 1010 | D2 | 2ND DIFF. VALUE |
| 1011 | P0 | INTRAOCULAR PRESS |
| 1100 | CV | C VALVE |
| 1101 | FV | FLOW VALVE |

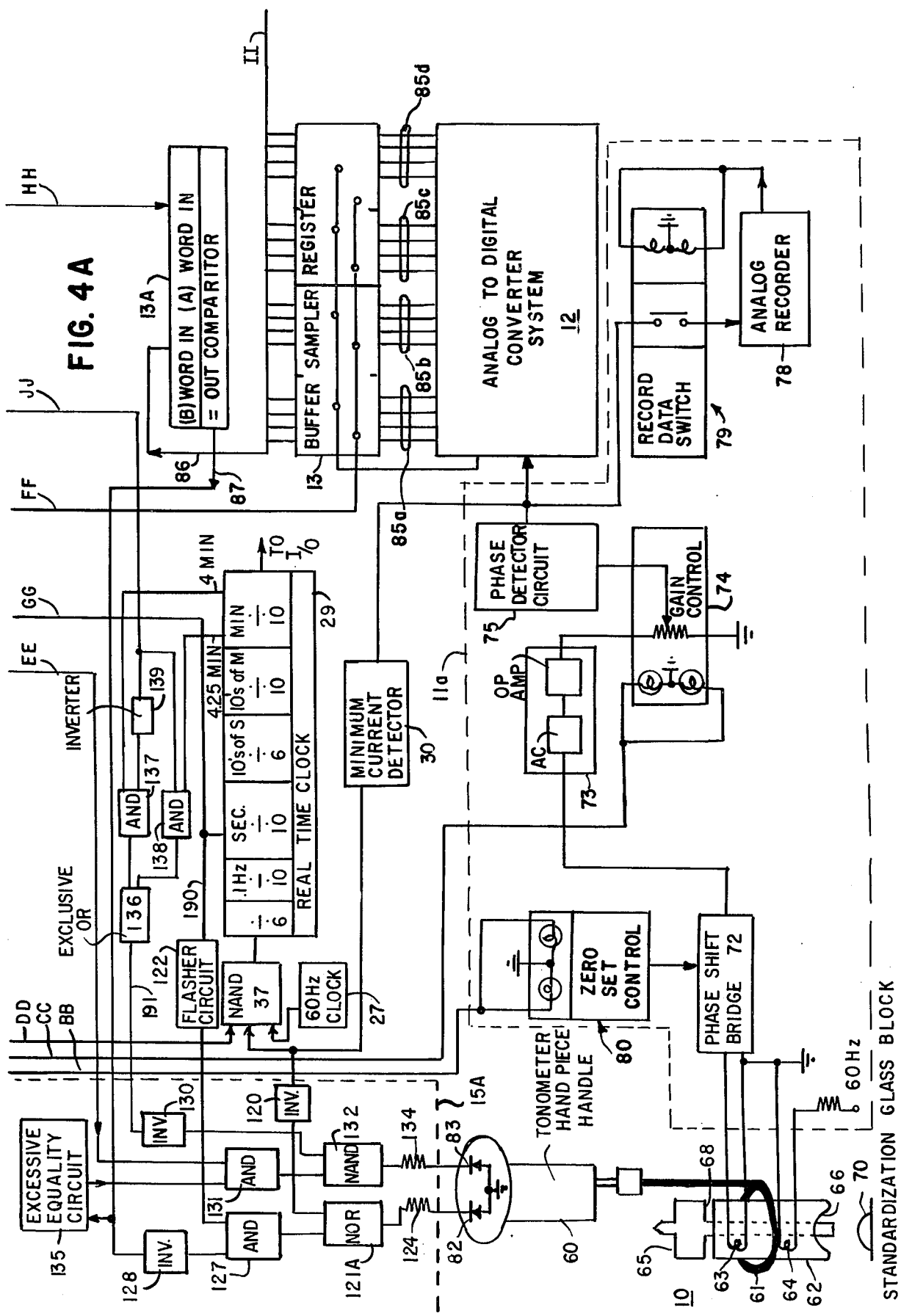

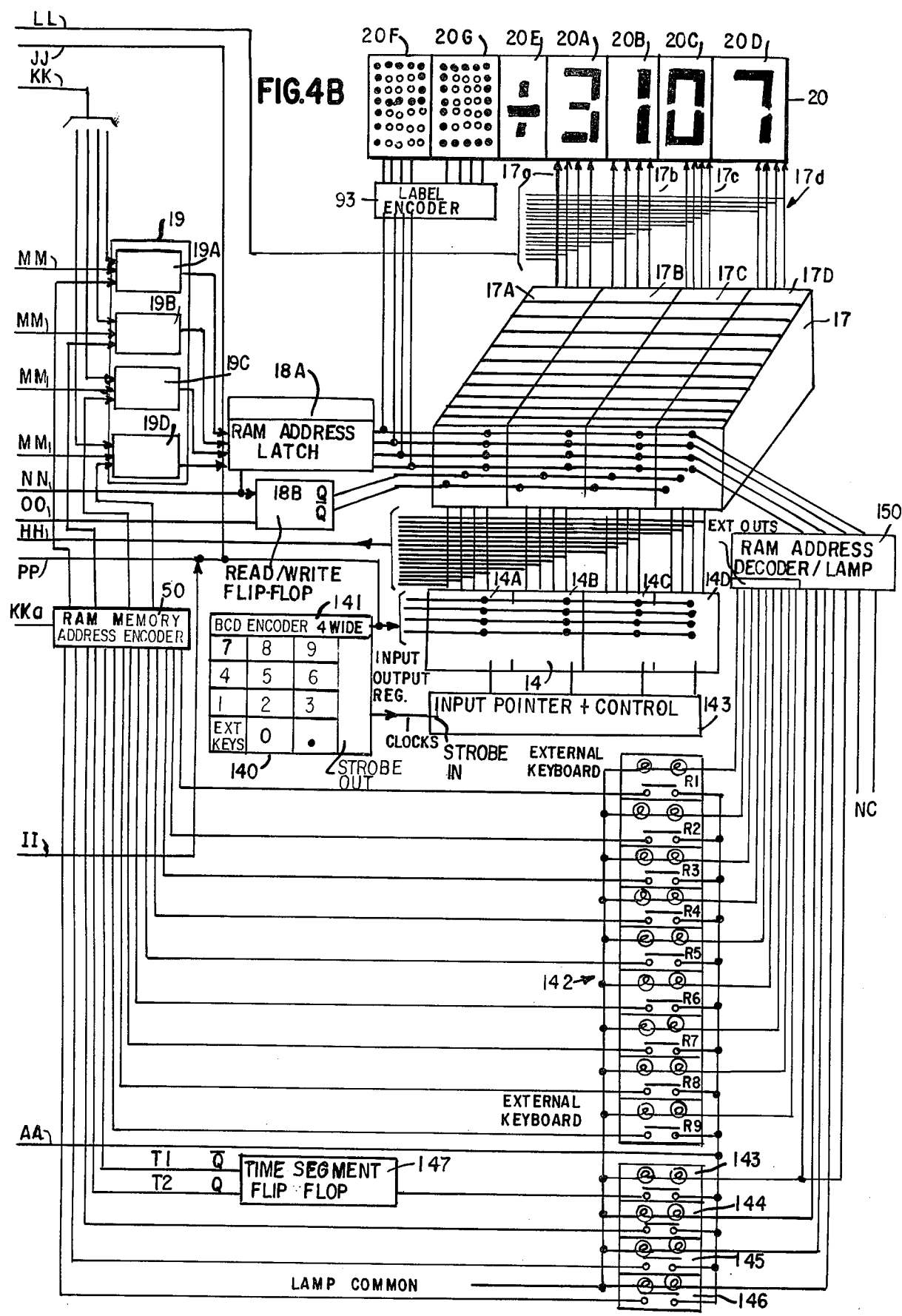

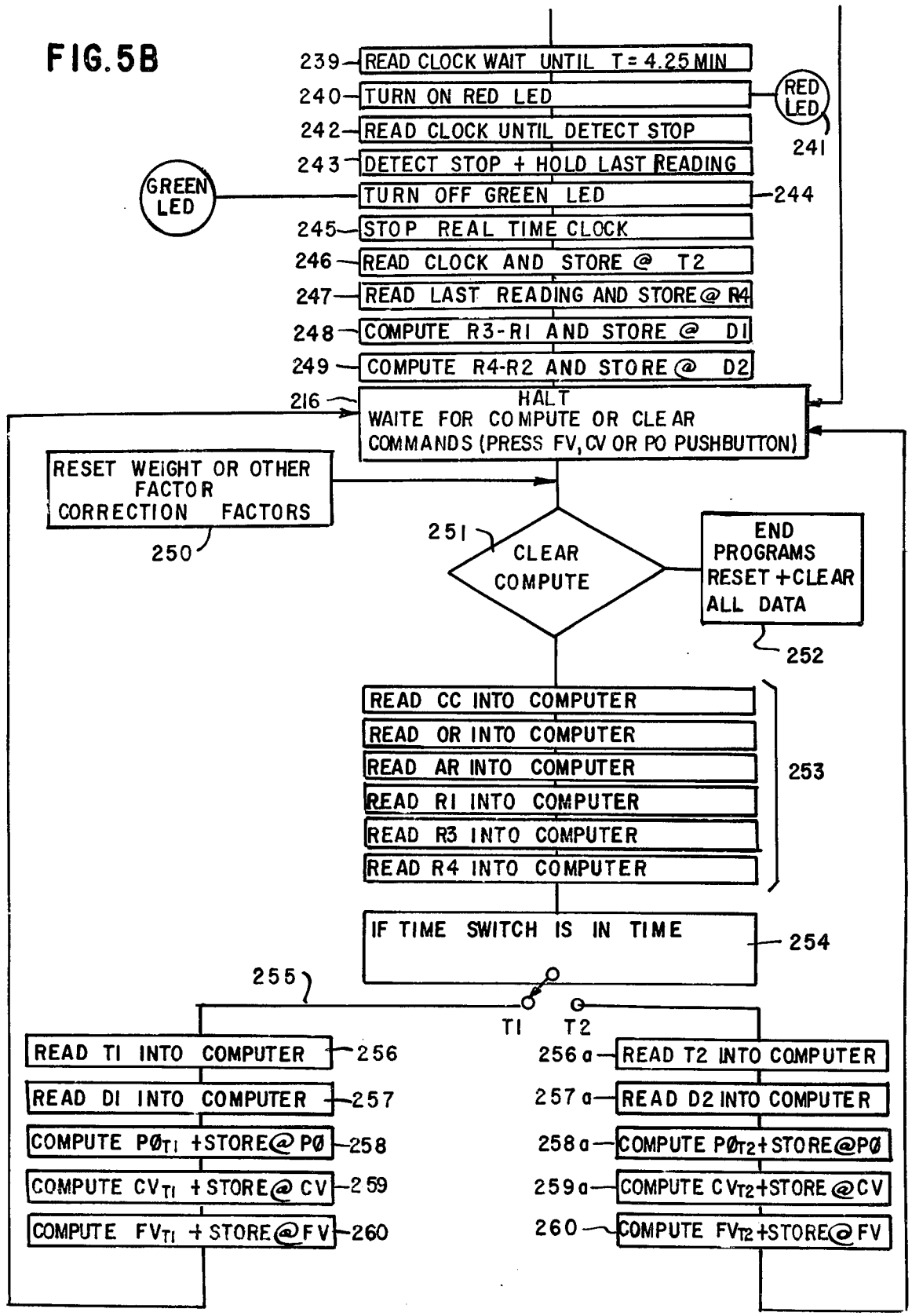

AUTOMATIC COMPUTING OCULAR TONOMETER SYSTEM

BACKGROUND AND SUMMARY

The present invention relates to an automatic computing tonometer system and method; and more particularly, it relates to a computerized ocular tonometer and a method of recording tonometry measurement data and computing the required test results which include the intraocular pressure, the "C" value and the flow value for an eye under test. The invention also relates to a unique tonometer handpiece which gives a clinician visual information relating to the test and results.

Electronic tonometers and tonographers are known in the art. Examples of currently available systems include the model OP9100 Inkles Tonographer and the Model OP9102 Electronic Tonometer, both manufactured by V. Mueller and Company, Chicago, Ill. Each of these instruments includes a tonometer handpiece which, as will be described in greater detail within, has a member, referred to as a "plunger" which rests on the eye under test. The weight of the plunger is known. The plunger will indent the surface of the eyeball under gravity, and the indentation is resisted by the intraocular pressure.

The handpiece includes a transducer which is an electro-mechanical device which generates an electrical signal, the phase of which is representative of the position of the plunger relative to its initial position.

As will be explained in more detail within, this signal is fed to a phase detector which generates an output signal having an amplitude representative of plunger displacement. This signal may be displayed on a meter having a scale measured in tonometric units, or it may be recorded, as on graph paper. In either case, it is not the actual measurement or graph which provides the useful or desired test results; rather, the test results such as intraocular pressure, P0, the C value CV, and flow value FV, are calculated from the displacement measurements, together with other information such as Corneal Curvature (CC), Ocular Rigidity (OR), and Aplanation Reading (AR). These other parameters are sometimes referred to herein as "Other Test Parameters". The actual calculation of the results may involve considerable table look-up, in addition to actual computation.

The test results may be greatly affected by various known artifacts, and if extreme accuracy is required, certain correction factors should be taken into consideration. One such artifact is a transient pressure within the eye caused by a temporary increase in blood pressure which may accompany placing the instrument on a subject's eye.

Because of the difficulty in eliminating the effects caused by these artifacts and the time required to determine the correction factors in using pencil and paper or a hand calculator, they usually are not made. The resulting computations of intraocular pressure, C value, and flow value are, therefore, not as accurate as they might be.

In its broader aspects, the present invention uses a high-speed digital computer with a conventional tonometer head (transducer) and measuring circuitry for computing very accurate results for interocular pressure, C value and flow value, eliminating artifacts and applying correction factors with or without operator intervention. For example, based upon Aplanation readings made before the test is conducted, the aplanation measurements may be fed into the system, and values of ocular rigidity, corneal curvature, and intraocular pressure may be computed accurately and rapidly. The more accurate results show up, of course, in the computed results for C value and flow value since these depend on the corrected test parameters and intraocular pressure. Thus, one of the principal advantages of the present invention is that the computer results are more accurate than have heretofore, in general, been produced in the past due to the extremely complex and difficult hand calculations required for correction factors. Further, a decision as to whether or not to include these correction factors is taken out of the hands of the clinician and automatically incorporated into the computation of end results. Still further, artifacts such as the initial pressure increase due to anxiety are eliminated automatically, as will be discussed. The speed of computation is so great that, for all practical purposes, the results are available immediately after test.

The digital computer used as an element in the inventive system is a programmed digital computer because such computers are readily available on the market at reasonable value and because of the great flexibility in the use of such computers. However, the programming is incorporated into the machine when sold, and even though it may be modified or replaced completely on a machine in the field, no programming is required of the clinician, although he may enter data by means of a keyboard. A fixed-wired computer may equally well by employed with the present invention, as persons skilled in the art will appreciate. However, some flexibility may be lost, and as mentioned, programmable computers with sufficient capacity are available at reasonable cost.

Each test is carried out under control of the computer which is driven by a real time clock. The clock is actuated in response to placing the tonometer in test position on an eye. The computer takes the tonometer measurements at predetermined times, as determined by the Real Time Clock, and stores the data in a Random Access Memory, together with signals representative of the other test parameters. From this data, the computer calculates interocular pressure, the C value and the flow value, incorporating correction factors as needed and eliminating artifacts. These computed results are also stored in the memory. An important aspect of the present system is that it is totally flexible and easily capable of adapting to new computations or corrections as the field progresses.

A keyboard which is used to enter the other test parameters into the system may also be used to enter tonometer test measurements, for example, from a previous test. In this case, the computer may likewise be used to compute interocular pressure, C value, and flow value. This feature may be invaluable to a research technician going back into medical archives in performing basic research.

Because the present invention contains a Real Time Clock which keeps track of the tonometer readings and records the time of each reading for calculating the end results, it is possible to abbreviate most tonograms from the conventional four-minute period to a shorter period, such as two minutes. This, of course, would reduce the overall time required for testing, and particularly that portion of the test in which a plunger rests on the patient's eye.

As mentioned, the measurements and results of a given test, together with the other test parameters, are stored in memory. This gives the clinician the ability to speculate on the results of a given test by altering the measurement values for other test parameters (to account for various correction factors) on a trial basis, then computing the end results again. By studying whether or not the various combinations of correction factors effect the end result, the clinician can assure himself that the interocular pressure, coefficient of outflow, and flow value or correct under varying conditions.

The invention also includes a novel handpiece which has a pair of signal lights, preferably one is red and one is green. These lights are energized by control logic circuitry for indicating to the clinician taking the test the exact status of the test, whether the results being obtained are satisfactory, and whether current or old test data is stored in the memory. This is done without requiring that the clinician divert his attention from the handpiece which, it will be appreciated, is in contact with an eye during test. Thus, in addition to the greater accuracy afforded by a high-speed digital computer, the substantially reduced computation time, the elimination of artifacts and the automatic incorporation of correction factors, the present invention has significant operational advantages over the prior art.

Other features and advantages of the present invention will be apparent to persons skilled in the art from the following detailed description of a preferred embodiment accompanied by the attached drawing wherein identical reference numerals will refer to like elements in the various views.

THE DRAWING

FIG. 3 illustrates a representative tonograph;

Figure 4C:
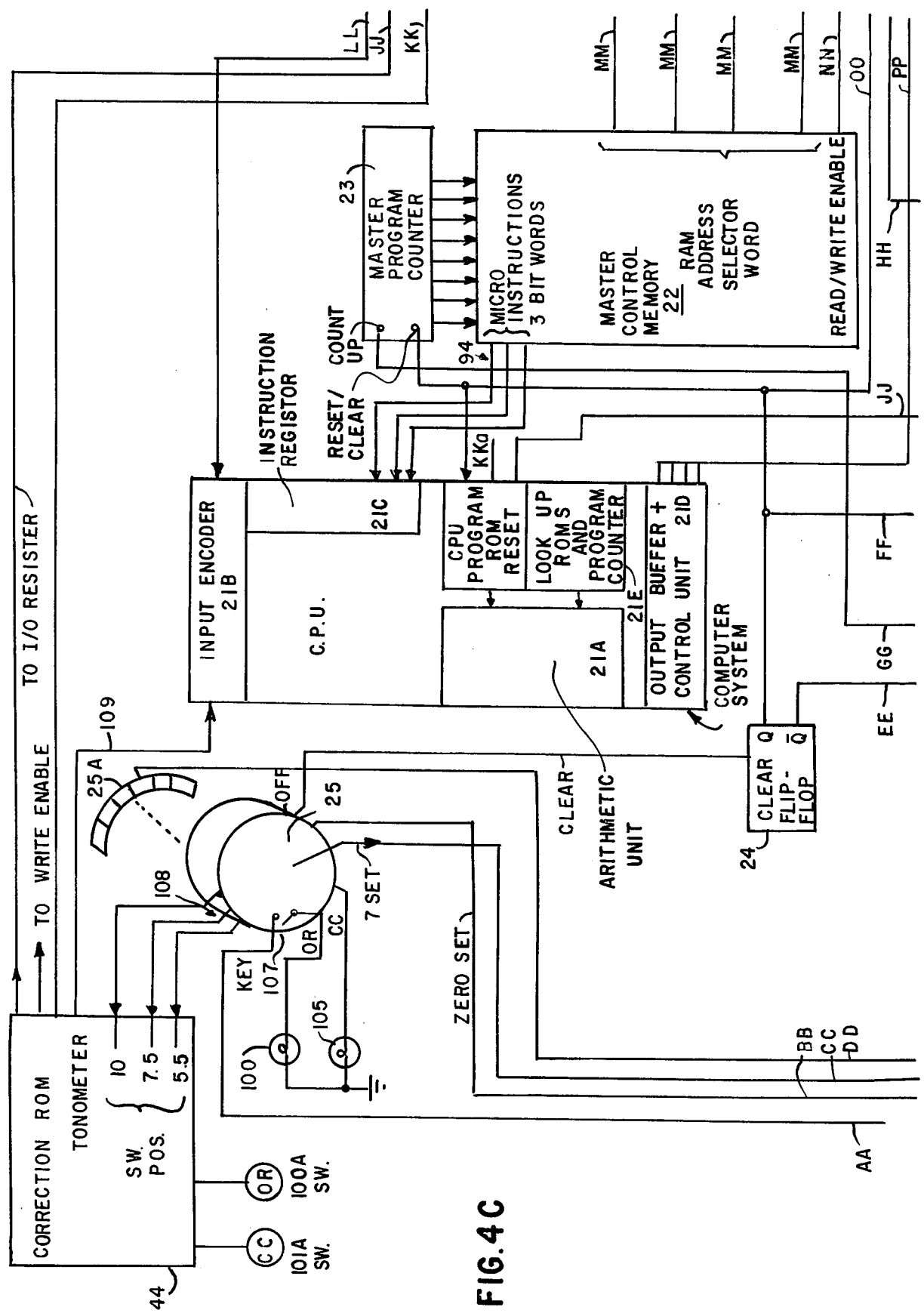
Figure 5A:
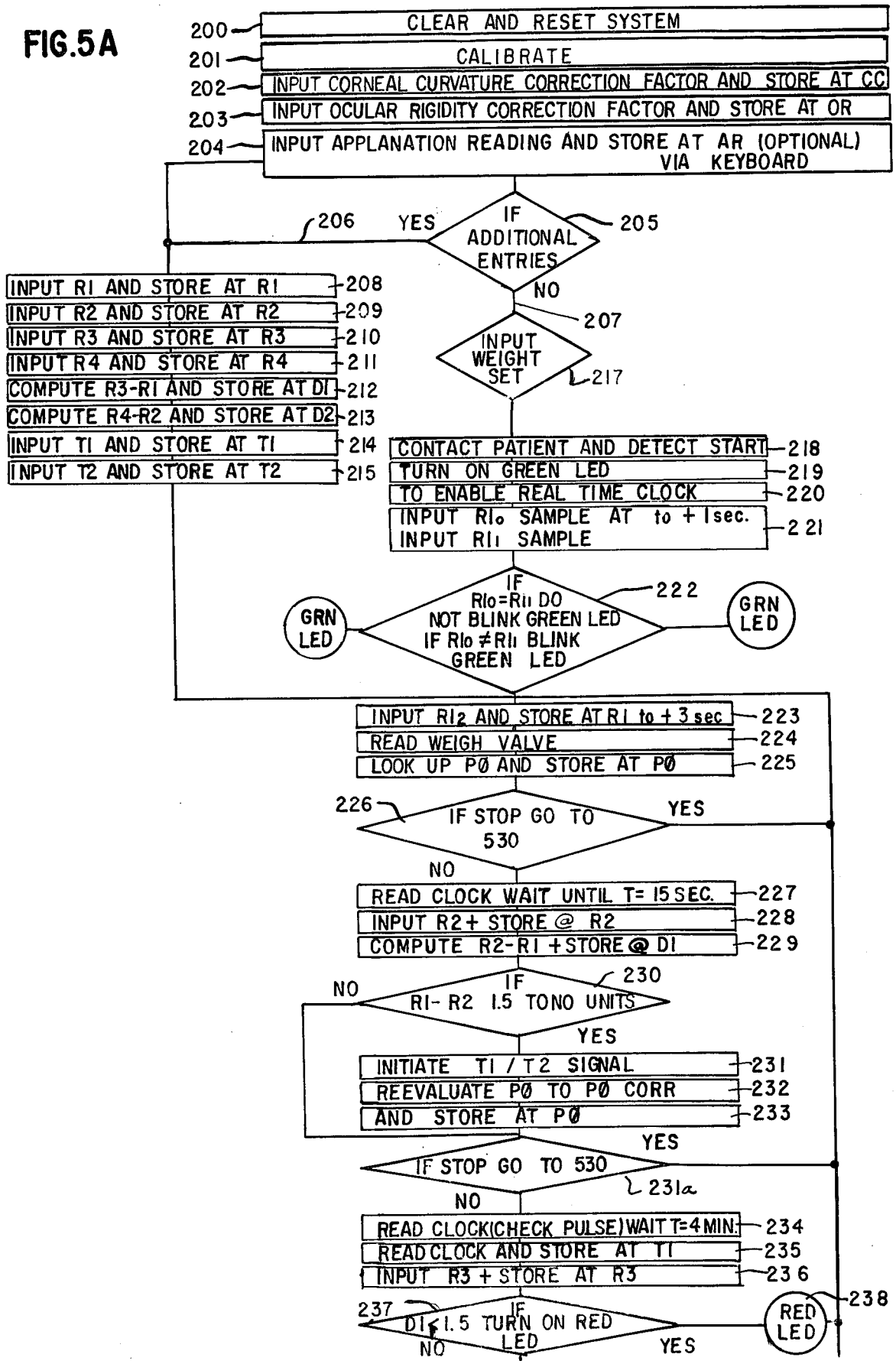

FIGS. 4A–4C comprise a detailed functional block diagram of the system;

FIGS. 5A–5B are detailed flow charts illustrating the programming of the computer used in the present invention;

FIG. 6 is a diagrammatic sketch illustrating the visual signals on the tonometer handpiece; and FIG. 7 is a table illustrating the various test readings, other test parameters, and computer results, together with their associated storage locations.

DETAILED DESCRIPTION

Before turning to the details of the system, it is felt that an understanding of the invention will be facilitated if the overall system operation and functioning are understood, together with the desired results. Turning first to FIG. 3, there is shown a typical tonograph represented by the wavy dark line T. In this graph, the abscissa is time and the ordinate is tonometric units which, in the illustration, increase in a downward direction so as to be inversely related to pressure. As will be discussed more within, the graph T is a measure of plunger displacement in a conventional tonometer transducer after the output signal has been converted to analog form. The present system takes tonometer readings at four different times; these are indicated as R1, R2, R3 and R4 respectively in FIG. 3. R1 is the initial reading—that is, it is taken when the test is begun, which as will be discussed, in the present system is when the circuitry detects that the tonometer transducer has engaged an eye being tested. The value at R2 is taken at a time after which any preliminary artifact, such as an elevated intraocular pressure due to anxiety, has subsided. This may vary depending upon experience, but a reading at about 15 seconds to 45 seconds after test initiation would be useful without unduly prolonging the test. In other words, R2 is the first test reading under normal circumstances without anxiety or squeezing; and for purposes of illustration it has been taken to be 0.25 minutes after start.

The reading at R3 is the final test reading, and if current practice is followed, this reading will follow the reading at R1 by four minutes. One of the features of the present invention, however, is that the reading at R3 may be advanced or adjusted according to the clinician's desire. The reading at R4 is a non-standard reading which is taken 4 minutes after R2. It is taken primarily as a safety measure and may be used, for instance, when it is thought that the preliminary portion of a test reading may have been rendered useless for some reason or other.

The four readings R1, R2, R3 and R4 are collectively referred to as the "test measurements". The test measurements, together with data indicating the corneal curvature, ocular rigidity, and aplanation reading (collectively referred to as the "other test parameter") are used to compute the end results—namely, intraocular pressure (PO), the coefficient of flow or C value (CV), and the flow value (FV).

OVERALL SYSTEM DESCRIPTION

Figure 1:
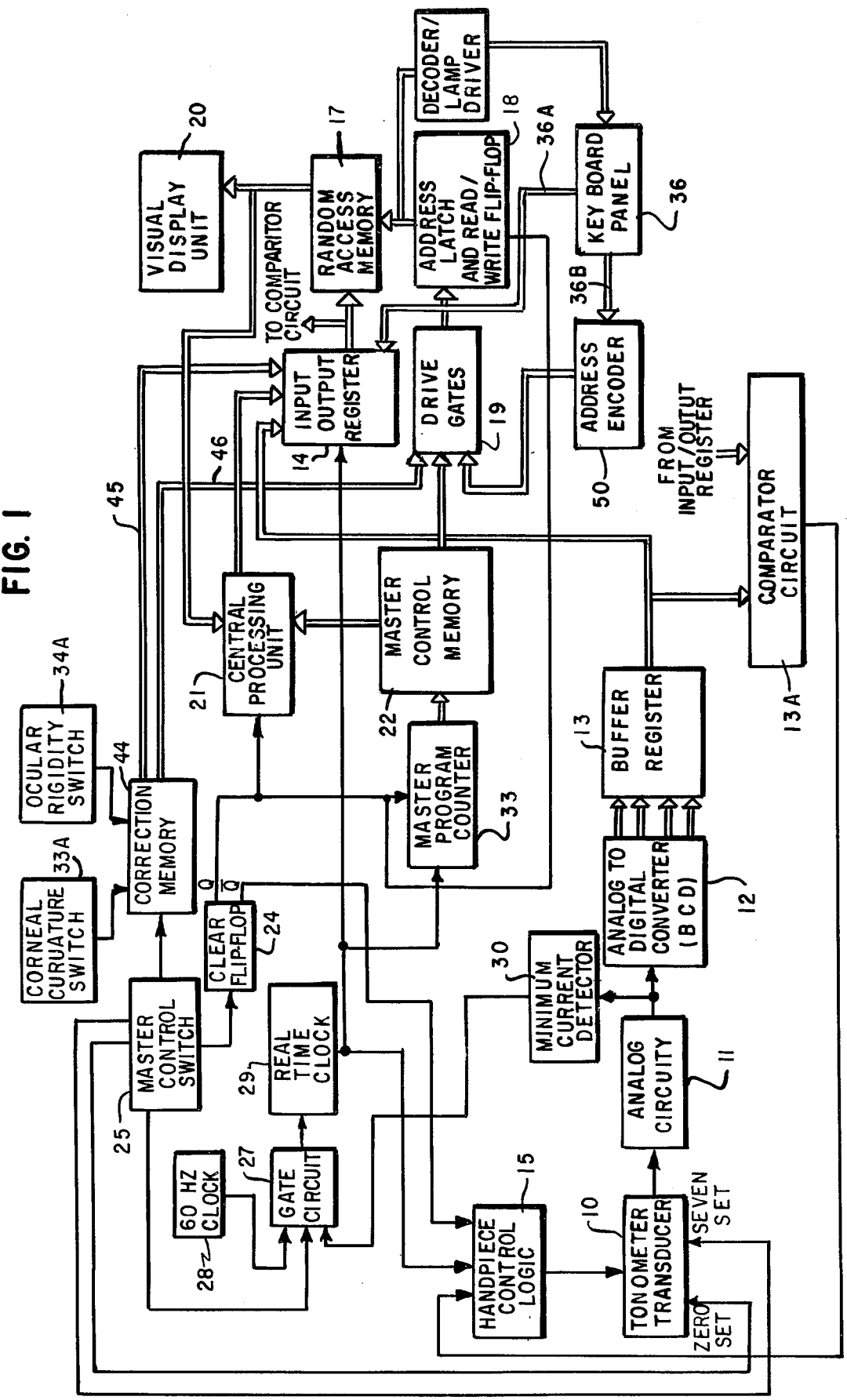
FIG. 1 is a functional block diagram of an automatic computing tonometer system incorporating the present invention.

Referring now to FIG. 1, reference numeral 10 generally designates a tonometer transducer which generates an electrical signal, the phase of which represents the displacement of a plunger from an initial location. The displacement occurs as the weight of the plunger indents an eyeball upon which the transducer is placed in test position. This phase modulated signal is fed to analog circuitry 11 which generates an output signal having an amplitude which is representative of the displacement of the plunger, and the amplitude signal is similar to the graph T in FIG. 3 which is a recording of the output of the analog circuitry 11.

An analog-to-digital converter 12 receives the output signal of the analog circuitry 11 and converts it to digital form, more particularly, to binary coded decimal form wherein the four most significant decimal digits are individually converted to binary representation. The system may easily accommodate more decimal places for greater accuracy, if desired. The binary coded decimal signals are temporarily stored in a Buffer Register 13, the output signals of which are connected to one side of a Comparator Circuit 13A and to an Input/Output Register 14. The Comparator Circuit compares the output of the buffer register 13 with the output of the Input/Output Register 14, the former representing a current reading and the latter representing the immediately previous reading. The output of the Comparator Circuit 13A is a signal which is present only when the two input words are identical, thereby indicating that two successive tonometer readings are equal. This is taken as an indication that the tonometer plunger is stuck, and a signal is transmitted to the handpiece control logic, generally designated in the block 15 to generate a signal which is readily visible to the operator while conducting a test to indicate that the plunger may be stuck.

The output signals from the Input/Output Register 14 are stored in predetermined locations in a Random Access Memory 17. The storage locations within the Random Access Memory 17 are determined by a RAM Address Latch 18 and associated circuitry which includes a Read/Write Flip-Flop for determining whether the data signals are being written into memory or retrieved from memory. As will be explained in more detail presently, drive gates 19 control the address latch 18 for addressing locations within the Random Access Memory (RAM) 17.

The output signals of the RAM 17 are coupled to a visual display unit 20 and to a Central Processing Unit 21 which contains the arithmetic and logic circuitry for computation and decision making. A Master Control Memory 22 contains the instructions for controlling the operation of the system, and these are fed to the Central Processing Unit 21. The timing for the execution of the instructions is determined by a Master Program Counter 23 which is initiated and started by a Clear Flip-Flop 24, and more particularly, the Q output thereof. The Q output of the Clear Flip-Flop 24 also initiates the Read/Write Flip-Flop associated with the Address Latch 18 for setting the Random Access Memory 17 to a READ condition, whereby the system is set to store new data from a test.

Turning now to the upper left-hand portion of FIG. 1, a Master Control Switch 25 is manually actuated by the clinician or technician taking the test to control the acquisition of test data, to feed information into the system, and to perform other test and control functions, as will be discussed. For example, prior to each test, the Master Control Switch will be set to a "clear" position for actuating the Clear Flip-Flop 24 to generate a signal on its Q output to reset the Master Program Counter 23, to initialize the Central Processing Unit 21, to reset the Address Latch 18 and place the Read/Write Flip-Flop in a WRITE state. As this time, a signal is also generated by the Master Control Switch 21 to inhibit a gate circuit 27 from communicating the output of a 60 Hz. Clock 28 to the input of a Real Time Clock 29. A second inhibit input of the Gate Circuit 27 is received from a minimum current detector 30 which receives the output signal of the analog circuitry 11 as presently discussed.

In the next two positions, the Master Control Switch 30 enables the clinician to calibrate the analog circuitry 11. This will be discussed in further detail when the analog circuitry is disclosed further. Next, the Master Control Switch (which is controlled by a knob 32 in FIG. 2) is set to positions for respectively entering data representative of corneal curvature and ocular rigidity for the subject under test. The actual settings are made by switches controlled by the knobs 33 and 34 respectively. The knobs 32, 33 and 34 are located on a faceplate panel P of a console generally designated 35 for housing the electronic circuitry. A keyboard generally designated 36 is coupled to the circuitry by means of a cord or cable 37, and it may be located as remotely as desired for convenience.

The panel P may be of a translucent material with an opaque packing except for two lines indicated in dash at 40 and 41. Continuous lines will be illuminated at the location indicated by 40 and 41 respectively when the Master Control Switch knob 32 is turned respectively to the "corneal curvature" and "ocular rigidity" positions, thereby indicating to the clinician that data has to be entered respectively by the knobs 33, 34.

Returning now to the functional block diagram of FIG. 1, the knob 33 controls a Corneal Curvature Switch 33A, and the knob 34 controls an Ocular Rigidity Switch 34A, both of which feed a correction memory 44 for generating binary coded decimal words coupled to the Input/Output Register 14 along a first bus 45 and for transmitting address information to the drive gates 19 along a second bus 46. Next, the Master Control Switch Knob 32 is set to a position indicating the weight of the plunger being used in the tonometer transducer 10 which, as indicated, may be 5.5, 7.5 or 10 grams since these are the three most common weights presently used. A heavier weight would be employed, if it were known that the ocular rigidity or intraocular pressure of the eye of the patient under test were relatively high. Persons skilled in the art are already familiar with these types of judgments which are made with conventional tonometers and tonographers.

The transmission of pulses from the 60 Hz. Clock 28 to the Real Time Clock 29 are no longer inhibited by the Master Control Switch 25, but by the minimum current detector 30. When the tonometer transducer is placed in test position on an eye, the upward movements of the plunger will cause the analog circuitry 11 to generate an output signal which, in turn, will be sensed by the minimum current detector 30 to enable the gate circuit 27 to transmit clock pulses to the real time clock 29, and this initiates data acquisition by advancing the Master Program Counter 23 which had been enabled by the previously received pulse from the Clear Flip-Flop 24, discussed above. The system then makes the tonometer measurement. That is, the analog circuitry 11 generates a signal having an amplitude representative of plunger displacement as discussed. This signal is periodically converted coded decimal signals, depending upon the sampling rate of the analog-to-digital converter 12, and at the times indicated, the binary coded decimal values are stored for the readings R1, R2, R3 and R4. These signals are stored at locations in the Random Access Memory 17. In between readings, the comparator circuit 13A monitors successive samples and signals the operator via handpiece control logic 15 if the plunger gets stuck. Alternatively, the readings R1, R2, R3 and R4 may be entered into the system by means of the keyboard panel 36 which transmits the data to the Input/Output Register 14 along bus 36A and the address information along a bus 36B to an Address Encoder 50, the output of which feeds the drive gates 19.

With all of the test measurement data stored in the Random Access Memory 17, together with the other test parameters of corneal curvature (CC), ocularity rigidity (OR) and aplanation reading (AR), the clinician may now have any of the required end results computed by pushing respectively any one of the pushbuttons 51 for interocular pressure (P0), 52 for the coefficient of flow value (CV), or 53 for the flow value (FV). The Central Processing Unit 21 makes the required computation under control of the Master Control Memory 22 and transmits the results back to the Input/Output Register and stores the results in an appropriate location (as determined by the Drive Gates 19 and Address Latch 18) in the Random Access Memory 17. The results are displayed on the visual Display Unit 20, as seen in the upper right-hand corner of the panel P of FIG. 2.

TONOMETER TRANSDUCER

Turning now to FIG. 4A, the Tonometer Transducer 18 is seen in more detail as comprising a handpiece handle 60 which supports a retainer ring 61 which holds a footplate 62. A bifilar coil including a first winding 63 and a second winding 64 are held by the footplate 62, and a movable plunger 65 is slidably received in the footplate 62.

The lower portion of the footplate 62, designated 66, has a concave surface for engagement with the cornea of an eye under test. It will be observed that when a test is not being conducted, the plunger 65 is in its lowermost position, under force of gravity, with a shoulder 68 engaging the top of the footplate 62 and acting as a stop. When the concave surface 66 of the footplate 62 is placed on an eye under test, the plunger is immediately moved to its uppermost position relative to the test block, and thereafter gradually begins to indent the eye, being displaced from its uppermost position. The magnitude of the signal from the base line in FIG. 3 is, therefore, proportional to displacement from the lowermost plunger position, but the tonometric units are measured in terms of displacement from the uppermost position. Calibration is achieved by placing the transducer on a standardization glass block diagrammatically illustrated at 70.

The lower position of the plunger 65, as is known in the art, is provided with a ferrite slug, and the winding 64 is energized with a 60 Hz. voltage. The relative position of the plunger 65 (and particularly the ferrite core contained therein) effects a change in the phase of the voltage induced in the secondary winding 63. As the plunger indents the cornea, its downward travel brings about a phase shift in the voltage at the secondary winding 63. This signal is fed through a phase shift bridge 72 which comprises a part of the analog circuitry 11 of FIG. 1, which analog circuitry is enclosed within the closed dashed line 11a in FIG. 4A. The output of the phase shift bridge 72 is coupled to an AC operational amplifier 73, the output of which is fed to a gain control circuit 74, and in turn, to a phase detection circuit 75. As illustrated, the gain control circuit 74 may be a potentiometer.

Further details containing the analog circuitry just described may be obtained from co-owned U.S. Pat. 2,519,681, of M. Mages, entitled "Tonometer Head" issued Aug. 22, 1950. The resulting analog signal from the phase detection circuit 75 has an amplitude which is representative of the displacement of the plunger 65 from its lowermost position. This signal may be recorded on an analog recorder 78 which is switched into circuit by means of a record data switch generally designated 79. Also enclosed within the analog circuitry 11 is a Zero Set Control Circuit 80. This circuit, together with the Gain Control Circuit 74 which is referred to as a "Seven Set Control" are arbitrary settings known in the art for calibrating the tonometer transducer over a linear range. These calibrations correspond to the respective tonometric units. The zero position calibration is made with the tonometer head placed on a standardization glass block 70 referred to as a 16 mm. test block. In the present system, this calibration is made with the Master Control Switch 25 in the "Zero Set" position, the circuit 80 being actuated along line BB. It will be observed that FIGS. 4A–4C, taken together, comprise a complete detailed functional block diagram; and when a signal line extends from one of these drawings to the other, it is indicated by a double capital letter, such as BB. The tonometer handpiece handle 60 is provided with two light-emitting diodes (LEDs), designated respectively 82 and 83, and comprising a green and red LED. The LEDs 82, 83 generate visual signals on the top end of the handpiece handle 60 for displaying the status of the system and the test to an operator without diverting his attention from the test—that is, while the transducer 10 is in testing relation to an eye. The LEDs 82, 83 are energized by the handpiece control logic of block 15 of FIG. 1 and enclosed within the dashed line 15a of FIG. 4A, which will be discussed below.

The "zero" setting discussed above represents a start or initial position assumed by the plunger 65 when it is placed on the standardization block 70. This position corresponds to an output current of the Phase Detector Circuit 75 of approximately one millamp. The "seven set" position corresponds approximately to the midpoint of the position of the plunger 65 in its downward travel; and the corresponding current from the phase detector circuit 75 is approximately one-half milliamp. In general, there is a linear relation between the tonometer scale readings up to ten units (FIG. 3) and the output analog current of the Phase Detector Ciricuit 75. The magnitude of the output analog current decreases with the vertical position of the plunger 65, that is, the output current is at a maximum when the plunger 65 is in its uppermost position and the output current is at a minimum when the plunger 65 is at its lowermost, but the tonometric numbers increase.

DIGITAL SUBSYSTEM

The output analog signal from the Phase Detector Circuit 75 is fed to the input terminal of the Analog-to-Digital Converter 12 which may have a sampling rate of 60 cycles per second. As mentioned, the Analog-to-Digital Converter generates signals representative of the four most significant decimal digits in the illustrated embodiment, and each of these is converted to BCD representation. Hence, the output signals of the Analog-to-Digital Converter 60 are coupled by means of four separate four-bit buses 85a–85d to the input of the Buffer Register 13.

The Buffer Register 13 (which may comprise two 8-bit latch circuits such as those sold by Texas Instruments Incorporated of Dallas, Tex., under the designation SN 74100 integrated circuit) is enabled by a clock pulse along the line E from the A/D converter when the A/D Converter has data pulses to transmit to it. The Buffer Register stores a receiver digitalized word for one clock period, the clock pulses being received, the Real Time Clock 29 for both the A/D Converter 12 and Buffer Register 13. It may be cleared by a single clock pulse. As the next clock period, the word being stored in Buffer Register 13 is transmitted via bus II to the Input/Output Register 14 (FIG. 4B) which feeds the RAM 15, as discussed. This word is stored at the input of the Input/Output Register 14, but not transmitted to the output until it, in turn, is enabled. The Input/Output Register 14 is structurally similar to the Buffer Register 13 except in the manner in which it is cleared. The Buffer Register Comprises two 8-bit latch circuits with clear, such as those manufactured by Texas Instruments Incorporated of Dallas, Tex. under the designation SN 74116. That is, the latch circuits are arranged in series with two bistable circuits for each bit. An incoming bit is transferred to the first latch circuit, and a subsequent clock pulse transfers that bit to the output latch. It is sometimes referred to as a "dual quad latch" or 8-bit latch. The Buffer Register differs from the Input/Output Register principally in that the former can be cleared directly by the Clear Flip-Flop 24. The Input/Output Register 14, on the other hand, receives the output signals of the Buffer Register 13; and it is cleared when the cleared output (all 0's) of the Buffer Register are transmitted to its output stage.

The output signals of the Input/Output Register 14 are also coupled by means of a sixteen-bit parallel bus HH to one input of the Comparator Circuit 13A. The Comparator Circuit 13A may comprise four four-bit magnitude comparators such as those sold under the designation SN 7485 by Texas Instruments, Inc. Each individual comparator receives two four-bit inputs and generates an output signal only when the inputs are identical. The comparator 66 also receives, at its other input, the output of the Buffer Register 13, as discussed. The function of the Comparator Circuit 13A is to generate an output signal at the lead 87 when the signals stored in the Buffer Register 13A are identical to those stored in the Input/Output Register 14. Since these two words comprise time sequential samples from the A/D Converter 12, the equality signal generated on line 87 by the Comparator circuit indicates that the plunger 65 is not indenting properly, as will occur if it sticks. It will be appreciated that normally the plunger will ride up and down with the fluctuating blood pressure within the eyeball caused by a heartpulse with an overall down trend so that no two sequential samples are identical under normal operating conditions. The lead 87 is coupled to the Handpiece Control Logid 15, the function of which will be discussed later.

In brief summary of the operation of the digital subsystem thus far described, the A/D Converter 12 generates BCD output signals of four bytes, each having four bits and sometimes collectively referred to as a "word". These are loaded sequentially into the Buffer Register 13 and thence fed to the comparator 13A. At the same time, the output words of the Buffer Register 13 are loaded sequentially by means of enable signals into four display sections 14A-14D associated with the Input/Output Register 14 and each representing a separate digit. The Input/Output Register 14 is also the point at which external data is entered into the system from the Keyboard Panel 36, as will be discussed.

The output signals of the Input/Output Register are coupled directly to the data input leads of the Random Access Memory 17 (RAM). The RAM 17 may comprise four nondestructive read-out transistor-transistor logic (TTL) array of flip-flop memory cells, such as type SN 7489, sold by Texas Instruments Incorporated. Such elements are designated respectively 17A, 17B, 17C and 17D. Each memory element is a 64-bit Read-/Write Memory wherein the memory cells are flip-flop circuits. Each memory element is organized into 16 words of four bits each. Thus, the entire RAM is a 16 × 16 matrix, each memory element associated with a different digit display section 14A-14D of the Input/Output Register 14. Buffer Memory Inputs comprise four address lines (received from the RAM Address Latch 18A in FIG. 4B), for data inputs (received respectively from the section 14A-14D of the Input/Output Register 14) a Read Enable signal (the Q output of Read/Write Flip-Flop 18B), and a Write Enable signal (the $\overline{Q}$ output of Flip-Flop 18B). This permits the RAM 17 to be controlled for the entry and access of data. For reading the memory, once the address signals (for one of the 16 addresses) appear in binary form at the output of the RAM Address Latch 18A, and the address is decoded, the contents of that address only appear at the output lines of the RAM 17. The 16 output lines are again organized into four decimal digit locations, and these are denoted respectively 17a, 17b, 17c and 17d. The output lines 17a–17d are connected respectively to four digit locations 20A–20D of the Visual Display Unit 20, in order of decreasing significance. Immediately to the left of the digit display unit 20A is an algebraic sign indicator 20E, which may be fix-wired to indicate a "plus" sign permanently, since no negative numbers are encountered.

Each of the digit display units 20A–20D may be of the type sold under the designation MDA 6101, and the Digit Display Unit 20E may be of the type MDA 6001, sold by Monsanto Electronics Special Products, Cupertino, Calif. 95014. The two remaining display sections, identified respectively as 20F and 20G, display the label for the numeric information being displayed at the same time. A list of the test measurements, other test parameters and computed results stored in the RAM 17, and the associated labels and binary code is illustrated in FIG. 7. The two display untis 20F and 20G are 5 × 7 dot matrices of individual light-emitting diodes for displaying alpha-numeric symbols. Units such as those sold by Monsanto Electronics Special Products under the designation MDA 111 may be used for the display sections 20F and 20G. Each of the display units 20A–20D includes a light-emitting diode read-out display having its own BCD to 7-digit decoder and driver; and the units 20F and 20G are BCD to alpha characters, also with decoder and driver.

The output signals of the RAM 17 are also fed by means of bus LL to the Central Processing Unit 21 (FIG. 4C) for processing, as will be described later.

In summarizing the operation of the Random Memory Section, the RAM Address Latch 22 determins whcih of the 16 addresses or words of the RAM 17 is to be accessed for reading or writing. Each of these addresses or words of the RAM 17 may be thought of as extending into the plane of the page with wach address location being in a different plane parallel to the plane of the page. Hence, when a single address location is addressed all 16 bits for that address location appear on the output liens 17a–17d. That is, the same address location is selected for each of the four side-by-side bytes of the memory section 17A, 17B, 17C and 17D. The RAM Address Latch 18A includes an input labelled E for "enable" which is fed from the Master Control Memory 19 (FIG. 4C) along the line NM.

Once a particular address location (of the 16 available) is selected by the RAM Address Latch 18A, the state of the Read/Write Flip-Flop 18B determines whether the system will read out of the RAM 17 ($\overline{Q}$ output true) or right into the RAM 17 Q output true). As mentioned, the RAM 17 is a non-destructive memory, although the invention is not so limited.

Information being written into the RAM 17 is received from the data lines comprising the output lines of the Input/Output Register 14, as discussed. The output signals of the RAM 17 are fed directly to the individual display units 20A–20D where they are decoded and generate corresponding digital display signals. As mentioned, the Display Unit 20E is fix-wired to display a plus sign. The output signals of the RAM Address Latch 18A are fed to a label encodes 93 which decodes the incoming four-bit signal into an appropriate label as indicated in FIG. 7, and generates the corresponding binary coded signal to each of the inputs of the Display Units 20F and 20G. The label encoder 93 may be conventional diode decoding matrix or it may employ transistors for encoding and driving. Thus, the label encoder 93, together with the Unit Display Sections 20F and 20G informs the clinician of the reading, parameter or measurement whose value is being displayed in the remaining five display units 20A–20B. For example, if the third byte location is being read from the RAM 17, the label encoder 93 generates two sets of signals which uniquely display the alphanumeric term R3, for example, in the units 20F and 20G respectively so that the operator knows that the value being displayed in the units 20A–20D is the value for R3.

The RAM Address Latch 18A receives its input signals from the Drive Gates 19, comprising four individual NAND gates designated respectively 19A, 19B, 19C and 19D. This enables the addressing from three separate locations: (1) the Master Control Memory 22 via bus lines MM (FIG. 4C), (2) the Correction Memory 44 via four individual lines comprising bus KK (FIG. 4C), and the Address Encoder 50 (FIG. 4B) which enables input data to be fed into the system via keyboard panel 36 (FIGs. 1 and 4B). The encoder 50 may also employ conventional diode logic, as is known in the art.

The Master Control Memory 22 may be a READ ONLY memory; and it contains the instructions which are executed by the Central Processing Unit 21. The instruction signals are communicated to the Central Processing Unit 21 by means of bus 94. Since certain of the instructions call for reading or writing into the RAM 17, address information from the Master Control Memory 22 is transmitted along the four bus lines MM from FIG. 4C to the drive gates 19 of FIG. 4B. In addition, a READ/WRITE enable signal is transmitted along line NN to the READ/WRITE Flip-Flop 18B in FIG. 4B.

The instructions are sequenced according to the program as originally placed in the Master Control Memory 22, but the sequencing or indexing is caused by the Master Program Counter 23 which is stepped along by the Real Time Clock 29 (FIG. 4A) along line GG. The Master Program Counter 23 may be reset or cleared by the Q output of the Clear Flip-Flop 24 (which also clears the program READ ONLY Memory of the Central Processing Unit 21, as illustrated.

CENTRAL PROCESSING UNIT (CPU)

The CPU 21 may be, but need not necessarily be, a computer sold under the designation PPS 25 by Fairchild Semiconductor of Mountainview, Calif. The CPU includes an Arithmetic Unit 21A in which a plurality of predetermined arithmetic or logical functions such as adding, dividing, subtracting, table look-up, etc. may be performed. Input data is received from the RAM 17 via 16-bit bus LL (FIG. 4B), and stored in Input Encoder 21B. Instructions are received from the Master Control Memory 22 and decoded in an Instruction Generator 21C. The resultants or outputs are then transmitted to an Output Buffer and Control Unit 21D, and coupled via bus PP directly to the signal inputs of the RAM 17 (FIG. 4B). The CPU also has a Master Program Counter which is driven by the Real Time Clock in the illustrated embodiment, and Look-Up Read Only Memories 21E which are internal to the CPU and used, for example, to perform the various individual steps required for each of the arithmetic functions capable of being performed within the unit.

MANUAL CONTROL CIRCUITRY

Figure 2:
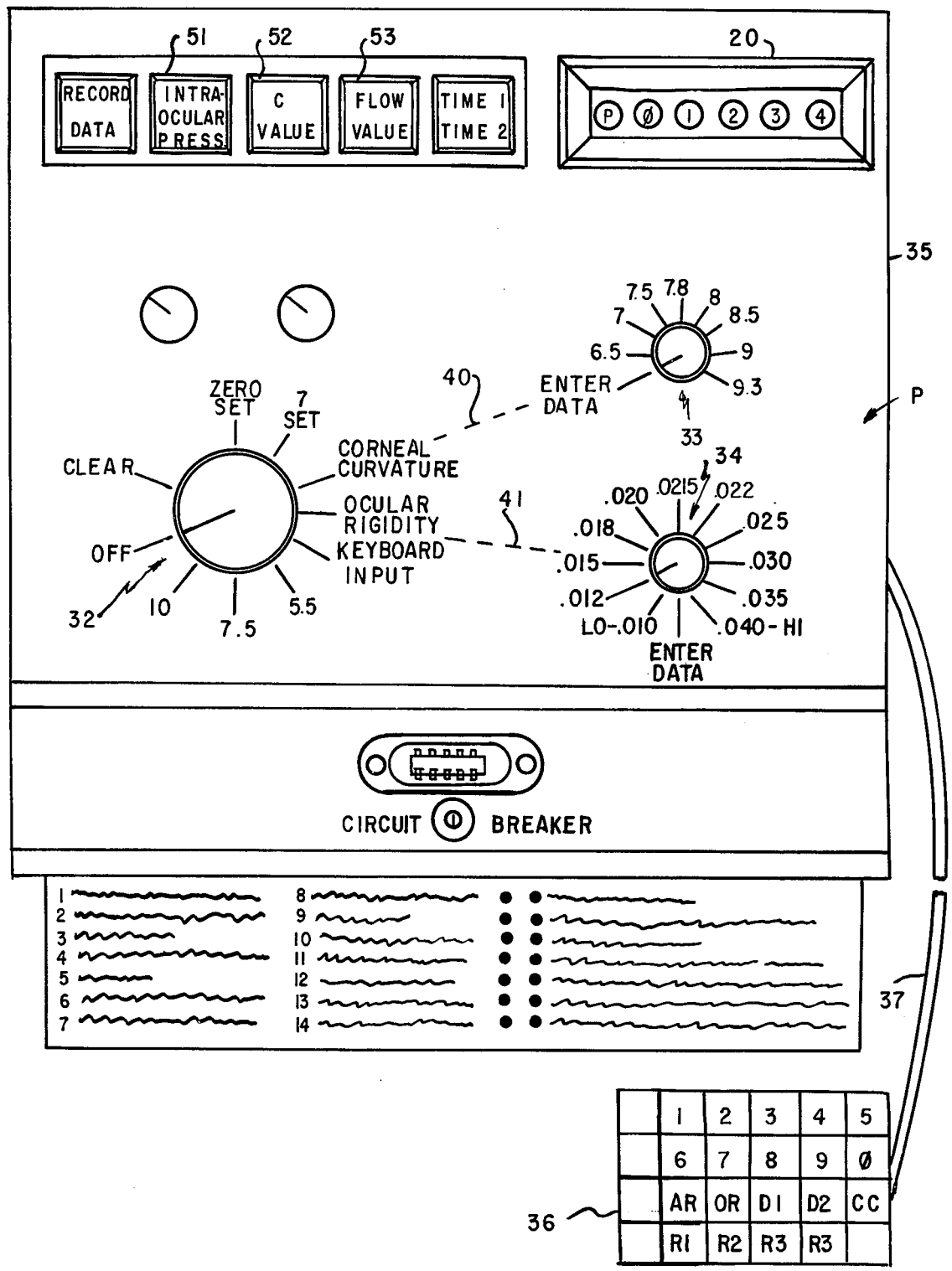
FIG. 2 is front view of a console and keyboard used with the present invention.

Turning now to the Master Control Switch 25 at the upper left-hand portion of FIG. 4C and as seen on the face-plate panel P of FIG. 2, it comprises a multi-deck rotary switch, one secondary deck being designated 25A. The second deck 25A is used to generate an inhibit signal (discussed presently) which is transmitted via line DD to one inhibit input of the gate circuit 37 of FIGS. 1 and 4A. Following in clockwise sequence are positions for OFF, CLEAR, ZERO SET and SEVEN SET which have all been explained except for the OFF position which is self-explanatory. The positions following the SEVEN set are labelled respectively CC and OR. These two positions are used respectively to enter the selected values of Corneal Curvature and Ocular Rigidity. These two values are selected by means of the knobs 33 and 34 in FIG. 2 which, in turn, control rotary step switches schematically shown respectively at 100A and 101A in FIG. 4C.

In either case, as will be discussed below, a first set of signals representative of the selected value of the parameter is coupled to the Correction Memory 44 and thence to the Input/Output Register 14 via bus JJ (FIG. 4B) for storage in the appropriate address location of RAM 15. A second set of signals, comprising fixed signals, represent the respective addressed into which the value data is to be stored in the RAM 15. The address information is generated by the Correction Memory 44 and fed to previously described Drive Gates 19 along bus KK.

Controls 100A and 101A, located on the front panel, are included as a convenience and must be relied upon in the absence of an external keyboard to input correction data for Corneal Curvature and Ocular Rigidity. The input correction factors from these controls is limited to the predetermined values labeled on the front panel. Should a more precise or intermediate correction figure be required, either of these two controls, or both, can be placed in the "enter data" position which effectively disables the automatic generation of a corresponding correction factors, and allows the corresponding RAM address to be directly accessed and programmed by the external keyboard. The CC, OR switches on the external keyboard address the Random Access Memory to the proper corresponding location for input of a specific correction factor for Corneal Curvature and Ocular Rigidity respectively. The function or the AR (applanation reading) serves a similar function.

When the Master Control Rotary Switch 25 is positioned in the CC position, a lamp 105 is also illuminated; and this lamp is located behind the translucent line 40 in the faceplate panel P in FIG. 2, connecting the CC position from the Master Control Switch to the knob 33 which sets the value for corneal curvature. This lamp also illuminates the various values that are capable of being set by the knob 33. Similarly, a lamp 106 (FIG. 4C) illuminates the second translucent line 41 interconnecting the position OR on the Master Control Rotary Switch and the knob 34 for setting a selected value of Ocular Rigidity, again, the particular values capable of being selected by the knob 34 also being illuminated.

The next position for switch 25, designated "KEY", is the position in which data may be manually entered into the system by means of the external keyboard 36. A ground is supplied by switch 107 along line AA to the keyboard switches of FIG. 4B, to be discussed below.

It will be recalled that an inhibit signal is generated by the second deck 25A of the switch 25. Such signal is generated when the switch 25 is in positions CLEAR, ZERO set and SEVEN set. The Gate Circuit 37 is a three-input NAND gate, and one signal input is the output of the 60 Hz. clock 27.

Turning now to the final three positions of the Master Control Rotary Switch 25, they are generally designated by reference numeral 108, and these comprise the three settable positions for selecting the test weight (i.e., weight of plunger 65), which informs the CPU 21 as to which weight value is being used during the test to indent the eye. These three positions are separate locations, as seen in FIG. 4C for the respective switch settings; and it will be appreciated that more weight positions could be used.

The selected weight value positions are wired directly to the CPU Input Encoder 21B by means of a bus generally designated 109. Having received the proper data for the selected weight, the system is now set up for making a computation if desired.

Assuming that the system is operating in the "normal" or "running" test mode, it will be observed that when the switch 25A is turned clockwise beyond the SEVEN set position, one inhibit input on the Gate Circuit 37 has been removed, but the Real Time Clock 29 is not yet running because the second inhibit input, received from the Minimum Current Detector 30 is still a ZERO signal—indicating, by virtue of less than a minimum current in the output of the phase detector 50, that the tonometer plunger 65 is fully extended, and resting on the shoulder 68. This, in turn, indicates that the transducer is not contacting the eye. A test begins when such contact is made by removing the inhibit signal from gate 37 and permitting clock pulses to be transmitted from the 60 Hz. Clock 27 to the Real Time Clock 29. The Minimum Current Detector 30 may incorporate conventional threshold circuit such as a Schmitt Trigger Circuit.

The Minimum Current Detector 30 has as its principal functions inhibiting operation of the Real Time Clock 29 until the Tonometer Transducer 10 is properly placed on the eyes, and terminating data acquisition at the end of a test. The first function is to be distinguished from the ZERO set position which is used to indicate that the plunger is in the upward position and to set the output current of the Phase Detector Circuit 75 to a normal one milliamp value. The clock is inhibited along the line DD when the switch 25A is in the ZERO set position in order to enable the operator to standardize the output signal of the phase detector 75. As the switch 25 is moved to the other, non-inhibiting positions, starting of the system computation is inhibited until contact is made with the eye under test by means of the transducer 10. As discussed presently, the Handpiece Control Logic 15 is also fed by the Minimum Current Detector 30; and this signal eventually energizes the green LED 82 in the top of the handpiece 60.

HANDPIECE DISPLAY AND CONTROL LOGIC CIRCUITRY

As seen in FIG. 4A, the Minimum Current Detector 30 also feeds an Inverter Circuit 120 in the Handpiece Control Logic Circuitry which in enclosed within the dashed line 15a. The output of Inverter 120 feeds one input of a NOR gate 121A which feeds cathode of the green LED 82 through a resistor 124. The other input of NOR Gate 121A is received from an AND Gate 127. Two inputs of the AND Gate 127 are received respectively from the comparator circuit 13A through an Inverter Circuit 128, and from the flasher circuit 122, which may be an astable multivibrator circuit triggered by the Real Time Clock 29. Ultimately, the Equality Signal on line 87 from Comparator 13A will, through the circuitry shown, energize the green LED 82 in the top of the handpiece 60. This light could either be flashing or continuous, as will be explained.

Still referring to FIG. 4A, reference numeral 130 denotes an Inverter Circuit which feeds NAND Gate 132, the other input of which is received from an AND Gate 131. The output of the NAND Gate 132 is connected by means of a resistor 134 to the cathode of the red LED 83. One input to the AND Gate 131 is received respectively from the $\bar{Q}$ output of the Clear Flip-Flop 24 (FIG. 4C) along line EE. The other input is received from the output of an Excessive Equality Circuit, designated by reference numeral 135 which is a sequential digital counter which counts the number of "equality" pulses received from the comparator 13A along line 87. Upon summing a predetermined number of such equality pulses, it will generate an output signal indicating that there is sticking of the plunger weight to such an extent that it will interfere with the results of the test.

The Inverter Circuit 130 is fed by an Exclusive OR Gate 136. One input of Gate 136 is received from AND Gate 137 and the other is received from AND Gate 138. The Gate 137 receives a signal from the Program Read Only Memory along line JJ through an inverter 139, which signal feeds the Gate 138 directly. The other inputs of Gates 137, 138 are received respectively from the 4.0 minute and 4.25 minute outputs of the Real Time Clock 29. The circuitry just described signals the end of a data acquisition period which, of course depends on whether the Central Processor has determined the presence of an artifact which will extend the test period the additional time of 0.25 minutes.

OPERATION OF HANDPIECE VISUAL INDICATORS

Normal operation prior to initiation of a test is indicated by both the red and the green LED lights 82, 83 being out. This indicates that the computer is clear and is illustrated on the top line LL1 of FIG. 6. When the handpiece is applied to an eye, the Minimum Current Detector 30 generates a signal which enables NOR gate 121A to pass a flashing signal (initiated by the 1 Hz. signal from the Real Time Clock 29) to flash the green LED, see LL3 of FIG. 6. This will continue during a normal test, unless it is overridden by the occurrence of an equality signal which will disable the AND Gate 127 via Inverter Circuit 128 and thereby inhibit the flashing signal from passing through, as indicated by line LL4. In this situation, the green light will be on continuously (state 4). If this state continues for a predetermined time, the Excessive Equality Circuit 135 generates an output signal (by virtue of having received too many equality signals), then the system passes to LL5 wherein the red LED flashes. The output of the Excessive Equality Circuit is derived from a free-running multivibrator to cause the red flashing.

Returning to state LL3, wherein the test is progressing normally, when a 4.0 or 4.25 minute output signal is generated by the Real Time Clock 37 (depending upon whether the computer has detected an artifact or the operator has specified the extended test period), the red LED 83 will be energized continuously (state LL6), indicating that the test period is over and the test has been successfully completed, but the gathering of information continues because the handpiece has not been removed from the eye. As soon as the handpiece is removed from the eye, the output of the minimum current detector 40 goes to zero, thereby disabling the green light completely, and it goes out; but the red light remains steadily lit (LL7) because the Clear Flip-Flop 24 (FIG. 4C) is in a $\overline{Q}$ state. The Clear Flip-Flop 24 will remain in this state until all data is cleared by means of the Master Control Switch 25.

If the system is in state LL7 and the normal clear positions are not effected by the operator to achieve state LL1, the red light stays on, but as s-on as the Minimum Current Detector is attached, the green light will flash, thereby placing this system in state LL2 of FIG. 6 and indicating to the operator that a test is in progress and everything is otherwise normal but the computer has not been cleared and that old data is still stored in the computer. This is an important advantage because the data stored in the computer may still be useful for the records of the subject just tested (not the new subject), and the operator is thus alerted to that fact. The Real Time Clock would not have been reset, and the system is not set up for a test because the program counters, etc. will also not have been reset.

KEYBOARD ENTRY OF DATA

Turning now to the external keyboard 36, it includes a conventional numerical keyboard section 140 (FIG. 4B), a BCD Encoder 141, and a plurality of manually actuated address switches, generally designated by reference numeral 142.

In order to enable the loading of data into the Input-/Output Register 14 by the keyboard 140, there is provided an Input Pointer and Control indicated by the block 143 which receives strobe and clock pulses from the external keyboard 140. The keyboard 140 enables a person to load information into the system manually by pressing the keys which are representative of numbers, each key closing a switch when depressed. The Input Pointer and Control 143 (which may be a "count four" circuit of bistables) steps an enable signal sequentially along the four decimal digit sections 14A-14D of the Input/Output Register 14 to supply sequential enable pulses for loading those digit sections individually. The keyboard also has an erase key for correction of input errors. It will be recalled that the A/D Converter 12 generates all four BCD digits simultaneously for loading into the Input/Output Register 14.

The adress switches 142 are each associated with a different parameter, meausrement or calculated result of the system. Thus, each of the switches 142 is directly wired to an input of a RAM Memory Address Encoder 50. There is one of the switches 142 associated respectively with each of nine parameters indicated in FIG. 7.

In addition, there are four switches 143-146 located on the faceplate panel P of FIG. 2, as distinguished from the keyboard panel 36. These switches are associated respectively with the remaining parameters and test results, and they represent respectively the calculated results T1 and T2 (collectively labeled TM and controlled by switched 143), FV (i.e., the Flow Value-Switch 144), CV (the coefficient of flow, switch 145), and P0 (the intraocular pressure, switch 146). The designator TM represents both parameters T1 and T2 (switch 143) and this switch signal is fed to a flip-flop 147 which converts it to a toggle signal so that the signals T1 and T2 may be transmitted alternately and exclusively along the lines which have been so designated to the RAM Memory Address Encoder 50.

Switches P0, FV, and CV as well as TM serve a dual purpose in that upon depression, each selects the corresponding address for P0, FV, etc., which enables the system to write into and concurrently read out data from the addressed location. Simultaneously, with the enabling of the corresponding computer address, the CPU reprocesses, computes and restores the information into the same address after processing. For example, depressing the P0 switch would allow the operator to input a P0 if nothing exists at that address. But once that data has been entered into the RAM, deparessing the same switch reprocesses all the information, redeposits it and makes correct corresponding RAM address and consequently displays it on the readout. The signal for starting computation is generated in the RAM Memory Address Encoder 50 (FIG. 4B) and coupled to the CPU Program ROM (FIG. 4C) via line KKa.

The remaining parameters, entered by means of the external keyboard 36, are also directly wired to the RAM Memory Address Encoder 50. Each of these switches is labelled with teh symbol of FIG. 7 for the measurement or parameter with which it is asociated. The RAM Memory Address Encoder 50 receives the various inputs (numbering 14 out of a possible 16) indicated in Table I and generates a four-bit binary signal which is representative of the associated address in the RAM 17 for the particular parameter being accessed or entered. The output leads of the RAM Memory Address Encoder 77 are coupled respectively to the four inputs of the NAND gates 19A-19D of the Drive Gates 19.

The encoded address signals are coupled from the Drive Gates 19 to the RAM Address Latch 18A which has already been discussed, and thence to the address portion of the RAM 17. The same signals are coupled to a RAM Address Decoder/Lamp Driver 150 which decodes the address information which actually appears at the RAM 17 and generates a signal along one of the 13 output leads, each of which is connected to a lamp associated with one of the switches 142, including both the keyboard switches and the panel switches 143-146. Thus, the clinician upon pressing one of the address switches 142 (either on the keyboard panel 36 or on the console panel P) is assured of proper addressing if the lamp associated with that particular address switch lights up because the information will have passed through the RAM Memory Address Encoder 50, the Drive Gates 19, the RAM Address Latch 18A, and the RAM Address Decoder/Lamp Driver 150.

In order to enter data, the clinincian first must turn the Master Control Switch Knob 32 to the KEY position to establish a ground for the pushbutton switches 142 along line AA (FIGS. 4B-4C). Next, he identifies the data if known that is being entered by pressing one of the pushbuttons 142 on the external keyboard panel 36 or one of the switches 143-146 located on the faceplate panel P of the console. This will generate an address signal in the manner already described for placement or replacement of the data in the preselected location in the Random Access Memory 17. After addressing the actual data is entered by pressing the individual numerical keys on the keyboard 140 in order of lesser significance so that the first digit pressed is the most significant, and it is routed through the BCD Encoder 141 and the Input/Output Register 14, and into the corresponding digit unit of the selected location of the RAM 17, as determined by the stepping of the Input Pointer and Control 143. The external keyboard 143, as mentioned, can be used only when the Master Control Rotary Switch is in the KEY position as shown in FIGS. 4C and 2, which closes the switch designated 107 of FIG. 4C.

As mentioned, each of the address switches 142 and 143-146 is a lighted pushbutton switch wherein the lamp is separately energized. Further, the switches are of the momentary contact type. The address leads for the RAM 15 are coupled to the RAM Address Decoder/Driver Section 150 which is a "one out of sixteen" Output Decoder/Lamp Driver—that is, each combination of binary input signal will energize a separate one of the output lines. The four right-hand output lines are coupled respectively to the lamps for the pushbuttons 143-146; and the remaining lines are coupled respectively to the lamps associated with the keyboard pushbuttons 142.

In addition to address checking, this enables an operator entering data manually to observe which data had last been entered. For example, if an entering data for R4, that pushbutton is depressed and the data entered, the RAM Address Decoder/Lamp Driver Section 150 will decode the address and energize the lamp associated with the switch R4, indicating to the operator that data had been entered or is being entered for that parameter. If the operator, knowing that the data entry has been completed, looks at the lighted switch, he knows that the next data to be entered is for the next-occurring unlighted switch. The Address Decoded/Lamp Driver Section 150 also transmits a signal from the RAM address encoder to the CPU to start computation of the selected function.

In the case of switch 143, the operator must also look to the alpha-numeric visual display sections 20F and 20G for information as to whether T1 or T2 is being entered; and he may depress the switch 143 if he desires to enter data for that parameter which is not being displayed. T1/T2 SN could also be a split lighted switch indicating first T1, then T2. That is, switch 143 together with the triggerable flip-flop 147 form a toggle action.

SYSTEM OPERATION AND DATA PROCESSING

Turning now to the system flow diagram of FIGS. 5A and 5B, there are initialization steps to be taken as represented by the block 200—Clearing and Reset the System. This is accomplished by means of the Master Control Switch 25 of FIG. 4C. In addition, a calibration is accomplished at 201. This includes the ZERO set and SEVEN set of the tonometer, as already discussed. Subsequently, the Corneal Curvature correction factor is entered and stored at CC in the RAM 17, as indicated by block 202. This is also accomplished in connection with the previously disclosed operation of the Master Control Rotary Switch, as are the steps in blocks 203 (Ocular Rigidity) and 204 (Aplanation Reading, if any). Entry of aplanation reading data, if available, is accomplished by means of the keyboard 140 and Address Switch 142 (AR)—that is, when the Master Control Switch is in the KEY position and the switch 142 labeled AR is depressed, actual data is entered by means of the keyboard 142.

The clinician then makes a decision in the decision block 205, depending upon whether he is going to perform a test on a patient or whether he is going to enter prerecorded tonogram information manually through the keyboard 140. In the latter case he pursues the route along line 206, and in the former, he proceeds along line 207.

In the case of entering the information by keyboard, the steps of data entry are spelled out clearly in the blocks 208-215, after which the system goes to a main termination block labeled HALT and designated by reference numeral 216.

If an actual test is to be conducted, the operator first sets the value of the weight being used, again using the knob 32 on the faceplate panel to set the Master Control Switch 25, this step being designated in block 217. He then contacts the patient's eye with the transducer; and the system, by means of the Minimum Current Detector 30 initiates operation as indicated in block 218.

The system then turns on the green LED 82 in a steady condition (block 219), and enables the Real Time Clock 29 in block 220.

The system then reads the stores the first sample of tonometric reading, block 221, identified $R1_0$. These steps, as well as the remaining steps are taken under program control. There are three preliminary values taken of $R1_0$, $R1_1$, and $R1_2$. These are taken at successive one-second intervals (the sampling period of A/D Converter 12) beginning at one second beyond $t_0$, (the time at which the Minimum Current Detector is actuated and the Real Time Clock is enabled). The one-second timing interval is taken from the 1 Hz. output of the Real Time Clock 29 which, as illustrated, generates a 1 Hz. timing signal on line 190 and a 4-minute signal on line 191. The reason for taking the first two samples ($R1_0$ and $R1_1$) is to make a determination as to whether or not the system is operating properly (which is determined by the presence of variation—i.e., in the Comparator Register 13A.

In other words, even though the initial samples are taken at a highly transient and almost meaningless time, nevertheless, the success of the testing is dependent on the fact that the plunger 65 is moving relative to the foot plate 62. The transiency of the signal at the very beginning is caused by the resiliency of the eyeball, and its accommodation to the weight of the plunger as the transducer is placed on the eye. Subsequent variations are caused by heart pulse and the reduction of intraocular pressure due to net fluid outflow from the eye.

In block 222, a determination is made as to whether the value of $R1_0$ is the same as $R1_1$. If they are the same, this is an indication that the plunger is not riding freely in the footplate, and a signal is generated to inhibit the blinking of the green LED, thereby indicating this to the operator. If the value of $R1_0$ is not the same as the value of $R1_1$, then the green LED is flashed by the Flasher Circuit 122, and this blinking indicates to the operator that the test is proceeding normally.

As the next block, 223, (namely three seconds after $t_0$), a reading is taken for R1 and this becomes the stored value of R1 (the initial tonometer reading in tonometric untis). Knowing this value of R1, an operator can go directly to a table and determine P0 provided the operator knows the value of the weight or has set the Master Control Switch to the proper position (5.5, 7.5 or 10), indicated in block 224, the look-up being denoted in block 225. These steps are performed by the computer, the table being stored in the Computer Look-Up ROM 21E, and the weight value having been fed into the computer at block 217 from RAM 17 under program control. The table just mentioned is a published table, well-known to those skilled in the art and sometimes referred to as the "Calibration Scale Approved by the Committee on Standardization of Tonometers of the Academy of Opthalmology and Otolaryngology" or the "1956 Schiotz Table" for short.

The data is stored in the Look-Up ROM 21E of the CPU 21 of FIG. 4A. The weight value (block 224) is determined from the position of the three available at 108 in which the Master Control Switch 25 is left.

Turning now to the decision block 226, the operator has the option to use the tonographer as a simple tonometer (that is, to compute the value of P0), in which case he would just terminate the test by removing the transducer from the eye and the program would proceed to the HALT block 216. If the test is to proceed, the program proceeds along the NO exit of block 226, and a reading is taken in block 227 at 15 seconds after $T_0$ (as determined by the Real Time Clock). This is in order to generate the measurement value for R2, the primary function of which is to eliminate any initial artifact that may have been caused by elevated intraocular pressure, usually due to anxiety. It will be observed that this 15-second delay from initiation may be varied, and in no way limits the invention.

In the next block 228, the 15-second reading is stored at location R2 in the RAM 17; and in block 229, a computation is made of the difference in tonometric units between the reading R2 and the reading R1; and this is stored as the value D1 in the RAM 17. In the next decision block 230, a determination is made as to whether the value R1 minut R2 is greater than a predetermined tonometric number such as 1.5. If the difference is not greater than 1.5 tonometric units, it indicates that the artifact is not present, and it is not necessary to re-evaluate the test. The operator, if he desires only to compute P0, may terminate the test by removing the transducer from test position, and the program exits by means of block 231. On the other hand, if the difference R1 – R2 (sometimes called D1) is greater than 1.5 tonometric units, the computer initiates a signal, designated TM (i.e., T1/T2) which extends the tonogram readings for a 15-second interval beyond the original 4-minute interval. The magnitude of the difference D1 is somewhat arbitrary and may be varied from the 1.5 value of tonometric units indicated.

If the value of D1 is greater than 1.5, the computer program in block 232 re-computes the value of P0, to $P0_{corr}$. This value is then stored at P0 location in the RAM 15, as indicated by block 233. For example, in the event that the difference D1 is greater than 1.5 tonometric units, thereby indicating the presence of an artifact at the initial point of the tonograph, the re-computed value of R1 for determining P0 may simply be the reading taken at R2 – 1.5 tonometric units, or re-evaluated on the basis of an aplanation reading (block 204), if available. The reason that 1.5 units are subtracted from the uncorrected value for P0, referring to FIG. 3 is that the readings are displayed in inverse order of tonometric units—that is to say, as the tonograph proceeds with time, the values of tonometric units increase.

In block 231a, if the operator decides to exit the program, he can calculate a value for P0, accounting for the initial artifact, thereby providing a more precise value of P0 if that is all he is interested in.

If the operator decides to proceed with the tonogram, the system just continues to read and convert the measurements from the transducer, and when the Real Time Clock generates a four-minute signal, block 234, the value of that time is stored at T1, in block 235—normally 4 minutes, although again not limiting the invention.

It will be observed that after the value for R2 is taken at 15 seconds, the system continues to read the Real Time Clock and the values for R3, and stores them at alternate time slots in the RAM 17. Hence, for each corresponding value of R3 that is stored in the RAM (see block 236) there is associated with it a corresponding time T1 at which it was taken. This operation will continue until the Real Time Clock reaches 4 minutes, at which time the CPU Program Read Only Memory (ROM) generates a signal to finalize the recording of R3 values, and the value of time T1 becomes fixed at 4 minutes.

Turning now to the decision block 237, if it were determined that D1 is less than 1.5, indicating most probably that an initial artifact was not present, the red LED 83 is turned on (see the circle 238) indicating that the test is complete. This corresponds to line LL 6 of FIG. 6.

If, on the other hand, in block 237 it has been determined that the difference D1 is greater than 1.5, then it would be desirable to extend the tonogram for a predetermined time; at which time the program proceeds to the instruction block 239 to extend the termination of the readings until 4.25 minutes (4 minutes, 15 seconds). Then, the red LED is turned on, see block 240 and circle 241.

Even though the red light is turned on, the operator may continue to leave the transducer in position until he notices the continuous red light, and during this time the clock is continued to be read in block 242 until the transducer is removed, at which time values will be stored in the RAM for R4 and T2, see the blocks 243, 244, 245, 246, 247, 248 and 249. In other words, these things occur almost simultaneously: the last measurement R4 is read; the green light 82 is turned off; the Real Time Clock 29 is stopped; the clock is read and stored at T2 in the RAM 17; a computation is made of the value R3 – R1 and stored at D1; and a computation is made of the value R4 – R2 and stored at D2 (see block 249).

At this time, the data-gathering is complete, and the HALT block 216 is encountered. The operator has the option of computing the various values or clearing the computer. In order to make the various computations, he presses a button on the faceplate panel (corresponding to one of the switches 143–146) according to what it is his desire to compute, such as FV or CV or P0. At this time, the operator can enter any correction values that he desires (see block 250)— such as resetting the weight value or the Corneal Curvature or the like. With these values all stored in the system, then, the operator proceeds to the next operational block 251 whereby he has two choices.

He can either clear the system (it will be observed that this is part of a loop and this provides a means of breaking the loop) at which time the loop is exited and the programs are ended, block 252. If the operator, on the other hand, decides to make a computation, depending upon the pushbutton (P0, CV or FV) that he presses, that value will be computed. However, before that time, certain recall functions are performed by the computer, retrieving data from the RAM. These are denoted collectively by the blocks 253, and include respectively reading values for CC, OR, AR, R1, R2, R3 and R4 into the computer, all from the RAM 15. In the next block, 254, the system determines whether the operator had set the TM switch to the T1 or the T2 position, T1 being indicative of his confidence that there is no initial artifact, and T2 being used if he thinks there was an initial artifact, conversely, he may use both of these positions, the information having been stored in either case.

If the time switch is set in the T1 position, the program proceeds along the line 255 to read T1 into the computer (block 256, read D1 into the computer, block 257, compute P0 at T1 and store the value in P0 of the RAM 258, compute CV at T1 and store the value in the CV position of the RAM 15, block 259, and compute the value of FV at T1 and store that value in the FV position of the RAM 15 (block 260). The program then cycles back through the HALT block 216, and the operator may again either insert additional corrections via block 50 or compute another value. The similar operation is conducted if the time switch is turned to the T2 position, as indicated correspondingly by the blocks designated 256A–260A.

As already discussed, the values stored in the RAM are displayed on the Visual Display Unit 20, as a function of the particular locations that are being addressed.

In summary, after the tonometer is placed on eye and R1 is measured, R1 is converted to P0 via the look-up table mentioned above, using the weight designation on which the master control switch is set. If P0 is in doubt, then an applanation reading can be entered via pushbutton AR which will override the R1 conversion to P0 and substitute P0 as measured by applanation. If CC and OR are set to normal then the computation proceeds as follows:

$$CV = \frac{AV}{T1 \text{ (average } P_T - P0 - PV)}$$

where:
T1 = Time in minutes from Real Time Clock.
PV = Episcleral venous pressure which is programmed and stored in the computer at the factory. It is adjustable, but would be set to equal 11.7.
P0 = Undisturbed intraocular pressure.
AV = Change in Ocular Volume and is stored in a Table Look-up and depends on scale reading on plunger load (weight), both known quantities.
AVE. $P_T$ = Average pressure during tonography which is also stored in a Look-up Table and depends on the scale reading and plunger load, both known quantities.

The flow, F, is computed from the following:
$$F = C (P0 - PV)$$
where:
C, P0, and PV are all stored in computer.
F = Flow of aqueous in micro liters per/minute.

If CC or OR are not normal than one of several known methods for correction can be employed. Such tables and corrections are, as mentioned, well known in the art and additional details can be obtained from the *SIMPLIFIED TONOGRAPHY*, Robert A. Schimek, M.D., (1960), published by V. Mueller & Co. of Chicago, Ill., which is incorporated herein by reference.

I claim:

1. An automatic computing tonometer system comprising: tonometer transducer means including a plunger slidably received in a foot plate and adapted for placement on a patient's eye, and further including circuit means responsive to the position of said plunger for generating an analog signal representative of the position of said plunger relative to said foot plate; analog-to-digital converter means receiving said analog signal for converting the same to digital signals representative thereof; memory means for storing said digital signals; read-out means communicating with said memory means for selectively reading the contents thereof and for converting the same to visual indicia; and programmed data processor means including clock means for storing said digital signal representations of said analog signal at predetermined times in said memory means during a test, said memory means further storing signals representative of test parameters, corneal curvature and ocular rigidity, said data processor means computing intraocular pressure at a predetermined time from said digital signals stored in said memory means.

2. The system of claim 1 wherein said data processor means further computes the coefficient of flow and the flow value from the data stored in said memory means and wherein said memory means further stores signals representative of an aplanation reading for the eye under test.

3. The system of claim 2 wherein said data processor means includes a Real Time Clock for controlling the same and for controlling the storage of said digital signals in said memory means at predetermined times in said test including signals representative of an R1 reading taken at the time said transducer means is placed in test relation on an eye and an R2 reading taken at a predetermined time thereafter, said data processor means computing a corrected value of intraocular pressure if the difference between said R1 and R2 measurements is greater than a predetermined amount, thereby indicating the presence of an artifact in the R1 reading, said artifact being representative of an elevated intraocular pressure.

4. The system of claim 1 wherein said tonometer transducer means includes circuit means for setting the SEVEN value and the ZERO value thereof, and wherein said system further comprises master control switch means selectively positionable by an operator in a plurality of positions including a CLEAR position, a ZERO set position, a SEVEN set position, a "corneal curvature" position, an "ocular rigidity" position, and a "tonometer weight" position, said system further comprising: clear circuit means responsive to said master control switch's being placed in said CLEAR position for clearing said data processor means; ZERO set control circuitry in said transducer means for setting the ZERO position thereof when said master control switch is in said ZERO set position; SEVEN set gain control circuitry in said transducer means for setting the SEVEN position thereof when said master control switch is in said SEVEN set position; circuit means including a first manually settable switch for generating digital signals representative of corneal curvature when said master control switch is ins said corneal curvature position and for storing said signals in said memory means; second circuit means including a second manually settable switch for generating signals representative of ocular rigidity when said master control switch is in said ocular rigidity position; and third circuit means for generating signals representative of a tonometer weight as set by the operator when said master control switch is in said tonometer weight position, and for storing said signals in said memory means.

5. The system of claim 4 wherein said master control switch futher comprises a KEY position, said system further comprising a manually actuated keyboard and circuit means responsive to keys depressed on said keyboard for entering data from said keyboard into said memory means representative of tonometric measurements and other test parameters.

6. The system of claim 1 wherein said tonometer transducer comprises a handpiece including a handle for holding said foot plate and said plunger and analog circuit means for generating said analog signal representative of the location of said plunger relative to said foot plate, said system further comprising first and second signal lights located on said tonometer handpiece handle; and handpiece control logic circuit means responsive to said clock and said analog circuit means for selectively actuating said first and second handpiece lights to indicate to an operator the condition of said system and the progress of a test without the operator's having to divert his attention from the test.

7. The system of claim 6 wherein said handpiece control logic circuit means turns off said first and second handpiece lights when said computer is clear and lights said first light steadily when said computer stores test values, and flashes said second light when a test is in progress.

8. The system of claim 7 further comprising minimum current detector means responsive to said analog signal for controlling said handpiece control logic circuit means when said plunger is removed from rest position to flash said second light, thereby indicating a test is in progress.

9. The system of claim 8 further comprising circuit means responsive to sequentially occurring digital signals of said analog-to-digital conversion means for inhibiting the flashing of said second light when sequentially occurring digital signal representations are equal.

10. The apparatus of claim 9 further comprising circuit means for flashing said first light when a predetermined number of said sequentially occurring digital signal representations are identical.

11. The system of claim 1 wherein said analog to digital conversion means further comprises encoder means for generating binary coded decimal signals representative of said test readings, said system further cr mprising input/output register means receiving said binary coded decimal signals for transmitting the same to said memory means at predetermined times and predetermined address locations under control of said data processor means.

12. The system of claim 11 wherein said memory means comprises a random access, READ/WRITE memory.

13. The system of claim 1 wherein said read-out means comprises visual display means receiving signals from said memory means for displaying digital signals representative of data and alpha numeric symbols representative of the parameter or measurement or result whose numerical value is being displayed.

14. In an automatic computing tonometer system, the improvement comprising: tonometer transducer means adapted to contact an eye under test for generating an analog signal representative of the indentation of a member placed on said eye;
real time clock means for generating signals representative of elapsed time; circuit responsive to said analog signals for starting said real time clock means when said analog signal is in a predetermined range indicative of said transducer means being placed in test relation in an eye; and digital circuit means under control of said real time clock means for converting said analog signals to digital representation and for storing the same at predetermined times in a test as determined by said real time clock means.

15. The system of claim 14 wherein said digital circuit means comprising analog-to-digital conversion means receiving said analog signal for converting the same to binary coded decimal representation; random access storage means; and data processor means responsive to said output signals of said real time clock means for selectively storing said digital signals of said analog-to-digital conversion means in preselected locations of said random access memeory means.

16. An automatic computing tonometer system comprising: transducer means including a plunger adapted for placement on an eye and slidably received in a footplate, and further including circuit means for generating an analog signal representative of the location of said plunger relative to said foot plate; analog-to-digital conversion means for converting said analog signal to digital signal representation at predetermined test readings, including an initial reading R1 and a second reading R2 taken a predetermined time after said initial reading, said predetermined time being longer than a normal period of artifact interference and shorter than a normal full test period; and data processing means responsive to said R1 reading and said R2 reading for comparing the same and for computing intraocular pressure based upon said R2 reading if the difference between said R1 reading and said R2 reading is more than a predetermined amount such as to indicate the presence of an artifact due to elevated intraocular pressure at the time said R1 reading was taken.

17. In a tonometer system including a tonometer transducer having a plunger adapted for placement on an eye and a foot plate slidably receiving said plunger, and analog circuit means for generating a signal representative of the location of said plunger relative to said foot plate, the improvement comprising: a handpiece for use by a clinician in placing said transducer means in test relation to an eye; visual indicator means on said handpiece and readily observed by said clinician without diverting his attention from a test; and handpiece control logic circuit means for controlling said visual indicator means to indicate to a clinician the status of the test.

18. The system of claim 17 wherein said visual indicator means comprises a first light and wherein said handpiece control logic circuit means comprises means responsive to said analog signal for lighting said first light when said transducer is placed in test relation on an eye.

19. The system of claim 17 wherein said circuit means includes means for flashing said light on and off during said test.

20. The system of claim 19 further comprising analog-to-digital conversion means for periodically converting said analog signal to digital representation, register storage means receiving said digital representations and for storing the same until said analog-to-digital conversion means converts the next sample to digital representation; comparison circuit means comparing the output signals of said analog-to-digital conversion means with said register storage means for generating an equality signal when said signals are identical, said handpiece control logic circuit means further comprising circuit means responsive to said equality signal for continuously lighting said first light.

21. The apparatus of claim 20 further comprising excessive equality circuit means responsive to said equality signal for counting the occurrence of the same and for flashing said second light of said handpiece when the counts stored therein exceed a predetermined number.

22. The system of claim 19 wherein said visual means further comprises a second light, said system further including memory means for storing test signals, said handpiece control logic means including cirucit means for continuously lighting said second light when said storage means is storing test data and for extinguishing said light when said storage means is clear.

* * * * *